United States Patent
Husby

(10) Patent No.: US 7,636,598 B2
(45) Date of Patent: Dec. 22, 2009

(54) CARDIAC DEVICE INTERFACE TO REDUCE VENTRICULAR PACING

(75) Inventor: Michael P. Husby, Chicago, IL (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 295 days.

(21) Appl. No.: 11/567,924

(22) Filed: Dec. 7, 2006

(65) Prior Publication Data

US 2008/0140147 A1    Jun. 12, 2008

(51) Int. Cl.
*A61N 1/00* (2006.01)

(52) U.S. Cl. .......................................... 607/9

(58) Field of Classification Search .................. 607/25, 607/9, 27, 30, 62, 17
See application file for complete search history.

(56) References Cited

U.S. PATENT DOCUMENTS

| | | | |
|---|---|---|---|
| 5,282,838 A | 2/1994 | Hauser et al. | |
| 5,334,220 A | 8/1994 | Sholder | |
| 5,372,607 A * | 12/1994 | Stone et al. | 607/30 |
| 5,487,752 A | 1/1996 | Salo et al. | |
| 5,540,727 A | 7/1996 | Tockman et al. | |
| 5,549,650 A | 8/1996 | Bornzin et al. | |
| 5,626,623 A | 5/1997 | Kieval et al. | |
| 5,713,930 A | 2/1998 | van der Veen et al. | |
| 5,741,308 A | 4/1998 | Sholder | |
| 5,861,007 A | 1/1999 | Hess et al. | |
| 5,891,176 A | 4/1999 | Bornzin | |
| 5,891,178 A | 4/1999 | Mann et al. | |
| 6,049,734 A * | 4/2000 | Lang | 607/9 |
| 6,167,307 A | 12/2000 | Hess | |
| 6,280,380 B1 * | 8/2001 | Bardy | 600/300 |
| 6,594,523 B1 | 7/2003 | Levine | |
| 6,597,951 B2 | 7/2003 | Kramer et al. | |
| 6,708,061 B2 | 3/2004 | Salo et al. | |
| 6,772,005 B2 | 8/2004 | Casavant et al. | |
| 6,792,307 B1 | 9/2004 | Levine et al. | |
| 7,010,349 B2 | 3/2006 | Conley et al. | |
| 7,013,176 B2 | 3/2006 | Ding et al. | |
| 7,096,066 B1 | 8/2006 | Turcott et al. | |
| 7,110,817 B2 | 9/2006 | Yu et al. | |
| 7,130,695 B2 | 10/2006 | Czygan et al. | |
| 7,324,844 B1 * | 1/2008 | Levine et al. | 600/510 |
| 2003/0078624 A1 * | 4/2003 | Carlson et al. | 607/9 |
| 2007/0129764 A1 * | 6/2007 | Burnes | 607/18 |

* cited by examiner

*Primary Examiner*—Scott M Getzow
(74) *Attorney, Agent, or Firm*—Schwegman, Lundberg & Woessner, P.A.

(57) ABSTRACT

A cardiac interface device helps program an implantable cardiac rhythm or function management device, such as to reduce unnecessary ventricular pacing to avoid contributing to the advancement of heart failure disease progression. An intrinsic conducted AV interval is measured for at least one heart rate, and is predicted or measured for other heart rates. One or more of an age-predicted upper rate limit, a measured sensed AV offset, a PVARP based on measured retrograde conduction time can be used to determine an AV search hysteresis control parameter, and a resulting ventricular interval is graphically displayed relative to the intrinsic conducted AV interval at various heart rates. Confidence intervals or percentage ventricular pacing can also be displayed. Separate graphs for sense and pace initiated AV intervals can be provided.

31 Claims, 7 Drawing Sheets

CARDIAC DEVICE INTERFACE TO REDUCE VENTRICULAR PACING

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2006, Cardiac Pacemakers, Inc. All Rights Reserved.

TECHNICAL FIELD

This patent document pertains generally to cardiac rhythm or function management devices, and more particularly, but not by way of limitation, to a cardiac device interface to reduce ventricular pacing.

BACKGROUND

Implantable medical devices include cardiac function management devices, such as pacers, cardioverters, defibrillators, cardiac resynchronization therapy devices, or devices having a combination of such attributes. Such devices generally use electrodes, such as for sensing intrinsic electrical heart signals, for delivering stimulations to induce heart contractions, or for delivering a countershock ("shock") to interrupt a tachyarrhythmia.

Cardiac function management devices are typically programmable. This allows a clinician or other user to establish proper values of one or more control parameters that control device operation, such as to tailor device functionality to a particular patient's needs. There are typically a plethora of device control parameters, which are typically subject to a complex set of sometimes interrelated rules constraining their values. This can make programming an implantable cardiac function management device to meet a particular patient's needs a daunting task for a clinician, who must typically operate within the demanding time-constraints imposed by our modern medical system.

Overview

Certain cardiac function management devices can provide, among other things, needed pacing energy pulses to a subject to evoke responsive heart contractions. This can help sustain the subject's metabolic need for cardiac output when the subject's autonomic nervous system is unable to do so. However, delivering a pacing pulse to evoke a responsive heart contraction when the subject's heart chamber would have contracted shortly thereafter anyway can, over a period of time, be deleterious. This is because excessive unnecessary ventricular pacing can advance the progression of congestive heart failure. Therefore, decreasing or minimizing unnecessary ventricular pacing can be helpful in avoiding such advancement of heart failure disease progression.

Example 1 describes a method of programming an implantable cardiac rhythm management device to avoid unnecessary ventricular pacing. The method comprises measuring an intrinsic conducted AV interval at a first heart rate or interval, wherein the intrinsic conducted AV interval is initiated by either a sensed or paced atrial contraction and is concluded by a sensed ventricular contraction. The first heart rate or interval is also measured. The method includes automatically measuring or automatically extrapolating intrinsic conducted AV intervals at heart rates or intervals that are different from the first heart rate or interval to determine a measured or predicted intrinsic conducted AV interval as a function of different heart rates or intervals, wherein the automatically extrapolating includes using the measured intrinsic conducted AV interval at the measured first heart rate or interval and the measured first heart rate or interval for performing the extrapolating. The method further includes automatically suggesting or automatically programming a dynamic AV delay interval, based upon the measured or predicted intrinsic conducted AV interval as a function of the different heart rates or intervals, such that the dynamic AV delay interval is longer than the measured or predicted intrinsic conducted AV interval at each of the different heart rates or intervals.

In Example 2, the method of Example 1 is optionally performed such that the automatically extrapolating the predicted intrinsic conducted AV interval as a function of different heart rates or intervals includes using a patient's age in performing the extrapolating.

In Example 3, the methods of any one or more of Examples 1 or 2 are optionally performed such that the automatically extrapolating the predicted intrinsic conducted AV interval as a function of different heart rates or intervals includes using information about the patient's health status in performing the extrapolating.

In Example 4, the methods of any one or more of Examples 1-3 are optionally performed such that the automatically extrapolating the predicted intrinsic conducted AV interval as a function of different heart rates or intervals includes using information about a recent myocardial infarction in performing the extrapolating.

In Example 5, the methods of any one or more of Examples 1-4 are optionally performed such that the automatically suggesting or automatically programming a dynamic AV delay includes providing a safety margin by at least which the dynamic AV delay is longer than the measured or predicted conducted AV interval at each of the different heart rates or intervals.

In Example 6, the methods of any one or more of Examples 1-5 are optionally performed comprising automatically suggesting or automatically programming an upper rate limit (URL) parameter using an age-predicted maximum heart rate or interval based on information about at least one of a patient's age or activity level, wherein the URL parameter includes at least one of a maximum tracking rate (MRT) or interval or a maximum sensing rate (MSR) or interval.

In Example 7, the methods of any one or more of Examples 1-6 are optionally performed comprising determining a sensed AV offset using a difference between (1) a first time interval between an atrial paced contraction and a ventricular sensed contraction during at least one first cardiac cycle and (2) a second time interval between an atrial sensed contraction and a ventricular sensed contraction during at least one second cardiac cycle.

In Example 8, the methods of any one or more of Examples 1-7 are optionally performed comprising automatically suggesting, automatically programming, or automatically displaying the determined sensed AV offset.

In Example 9, the methods of any one or more of Examples 1-8 are optionally performed comprising applying the determined sensed AV offset to the dynamic AV delay interval to obtain an AV-offset adjusted dynamic AV delay interval that is longer than the measured or predicted intrinsic conducted AV interval at each of the different heart rates or intervals.

In Example 10, the methods of any one or more of Examples 1-9 are optionally performed comprising determining a dynamic post ventricular atrial refractory period (PVARP), including measuring a retrograde conduction time between a ventricular paced contraction and a sensed atrial depolarization, and including establishing the dynamic PVARP to be greater than or equal to the measured retrograde conduction time.

In Example 11, the methods of any one or more of Examples 1-10 are optionally performed comprising automatically suggesting or programming the dynamic PVARP.

In Example 12, the methods of any one or more of Examples 1-11 are optionally performed comprising determining an atrioventricular search hysteresis (AVSH) control parameter that controls providing an extended dynamic AV delay interval to allow an additional time period for ventricular sensing, including constraining the AVSH control parameter by selecting the AVSH control parameter to limit the extended dynamic AV delay interval to be longer than a sum of a minimum value of the dynamic AV delay interval and a minimum value of the dynamic PVARP.

In Example 13, the methods of any one or more of Examples 1-12 are optionally performed such that the constraining the AVSH control parameter comprises selecting the AVSH control parameter to limit the extended AV delay interval to be shorter than an upper rate limit (URL) interval.

In Example 14, the methods of any one or more of Examples 1-13 are optionally performed comprising automatically suggesting or programming the AVSH control parameter.

In Example 15, the methods of any one or more of Examples 1-14 are optionally performed comprising graphically displaying to a user the AVSH interval as a function of heart rate or interval, together with the measured or predicted intrinsic conducted AV interval as a function of heart rate or interval.

In Example 16, the methods of any one or more of Examples 1-15 are optionally performed comprising graphically displaying to the user at least one of an indication of a safety margin by which the AVSH interval exceeds the measured or predicted intrinsic conducted AV interval or an indication of how much ventricular pacing is expected to occur.

In Example 17, the methods of any one or more of Examples 1-16 are optionally performed comprising graphically displaying to a user an indication of the dynamic AV delay as a function of heart rate or interval, together with the measured or predicted intrinsic conducted AV interval as a function of heart rate or interval.

In Example 18, the methods of any one or more of Examples 1-17 are optionally performed comprising graphically displaying to the user an indication of a safety margin by which the dynamic AV delay exceeds the measured or predicted intrinsic conducted AV interval or an indication of how much ventricular pacing is expected to occur.

In Example 19, the methods of any one or more of Examples 1-18 are optionally performed comprising displaying to the user a suggested or programmed maximum tracking rate (MTR) or interval value, a minimum AV delay value, a maximum AV delay value, a sensed AV offset value, a minimum post ventricular atrial refractory period (PVARP) value, a maximum PVARP value, and an AV search hysteresis value.

In Example 20, the methods of any one or more of Examples 1-19 are optionally performed comprising display of upper rate limit (URL) parameters, including at least one of a maximum tracking rate (MRT) or interval or a maximum sensing rate (MSR) or interval, and the option to manually input the desired values for extrapolation of the dynamic AV Delay and/or AVSH value, a Sensed AV Offset value, a minimum and maximum PVARP, and predicted AV conduction interval as a function of different heart rates or interval.

Example 21 describes an apparatus for programming an implantable cardiac rhythm management device to avoid unnecessary ventricular pacing. The apparatus comprises a means for measuring an intrinsic conducted AV interval at a first heart rate or interval, wherein the intrinsic conducted AV interval is initiated by either a sensed or paced atrial contraction and is concluded by a sensed ventricular contraction. The apparatus also comprises a means for measuring the first heart rate or interval. The apparatus also comprises a means for automatically measuring or automatically extrapolating intrinsic conducted AV intervals at heart rates or intervals that are different from the first heart rate or interval to determine a measured or predicted intrinsic conducted AV interval as a function of different heart rates or intervals, wherein the automatically extrapolating includes using the measured intrinsic conducted AV interval at the measured first heart rate or interval and the measured first heart rate or interval for performing the extrapolating. The apparatus also comprises a means for automatically suggesting or automatically programming a dynamic AV delay interval, based upon the measured or predicted intrinsic conducted AV interval as a function of the different heart rates or intervals, such that the dynamic AV delay interval is longer than the measured or predicted intrinsic conducted AV interval at each of the different heart rates or intervals.

Example 22 describes an apparatus for programming an implantable cardiac rhythm management device to avoid unnecessary ventricular pacing. The apparatus comprises an atrial sensing circuit, an atrial therapy circuit, a ventricular sensing circuit, a ventricular therapy circuit, and a controller circuit, coupled to the atrial sensing and therapy circuits and the ventricular sensing and therapy circuits. The controller circuit is configured: to measure an intrinsic conducted AV interval at a first heart rate or interval, wherein the intrinsic conducted AV interval is initiated by either a sensed or paced atrial contraction and is concluded by a sensed ventricular contraction; to measure the first heart rate or interval; to measure or extrapolate intrinsic conducted AV intervals at heart rates or intervals that are different from the first heart rate or interval to determine a measured or predicted intrinsic conducted AV interval as a function of different heart rates or intervals, wherein the extrapolating includes using the measured intrinsic conducted AV interval at the measured first heart rate or interval and the measured first heart rate or interval for performing the extrapolating; and to automatically suggest or automatically program a dynamic AV delay interval, based upon the measured or predicted intrinsic conducted AV interval as a function of the different heart rates or intervals, such that the dynamic AV delay interval is longer than the measured or predicted intrinsic conducted AV interval at each of the different heart rates or intervals.

In Example 23, the apparatus of Example 22 is optionally configured such that the controller is configured to automatically suggest or program a dynamic AV delay that includes a safety margin by at least which the dynamic AV delay is longer than the measured or predicted conducted AV interval at each of the different heart rates or intervals.

In Example 24, the apparatus of one or more of Examples 22 or 23 is optionally configured such that the controller is configured to automatically suggest or automatically program an upper rate limit (URL) parameter using an age-predicted maximum heart rate or interval based on information about at least one of a patient's age or activity level, wherein the URL parameter includes at least one of a maximum tracking rate (MRT) or interval or a maximum sensing rate (MSR) or interval.

In Example 25, the apparatus of one or more of Examples 22-24 is optionally configured such that the controller is configured to determine a sensed AV offset using a difference between (1) a first time interval between an atrial paced contraction and a ventricular sensed contraction during at least one first cardiac cycle and (2) a second time interval between an atrial sensed contraction and a ventricular sensed contraction during at least one second cardiac cycle.

In Example 26, the apparatus of one or more of Examples 22-25 is optionally configured such that the controller is configured to apply the determined sensed AV offset to the dynamic AV delay interval to obtain an AV-offset adjusted dynamic AV delay interval that is longer than the measured or predicted intrinsic conducted AV interval at each of the different heart rates or intervals.

In Example 27, the apparatus of one or more of Examples 22-26 is optionally configured such that the controller is configured to determine a dynamic post ventricular atrial refractory period (PVARP), including: to measure a retrograde conduction time between a ventricular paced contraction and a sensed atrial depolarization; and, to establish the dynamic PVARP to be greater than or equal to the measured retrograde conduction time.

In Example 28, the apparatus of one or more of Examples 22-27 is optionally configured such that the controller is configured to determine an atrioventricular search hysteresis (AVSH) control parameter that controls providing an extended dynamic AV delay interval to allow an additional time period for ventricular sensing, and to constrain the AVSH control parameter by selecting the AVSH control parameter to limit the extended dynamic AV delay interval to be longer than a sum of a minimum value of the dynamic AV delay interval and a minimum value of the dynamic PVARP.

In Example 29, the apparatus of one or more of Examples 22-28 is optionally configured comprising a display configured to graphically display to a user the AVSH interval as a function of heart rate or interval, together with the measured or predicted intrinsic conducted AV interval as a function of heart rate or interval.

In Example 30, the apparatus of one or more of Examples 22-29 is optionally configured to display to the user at least one of an indication of a safety margin by which the AVSH interval exceeds the measured or predicted intrinsic conducted AV interval or an indication of how much ventricular pacing is expected to occur.

In Example 31, the apparatus of one or more of Examples 22-30 is optionally configured such that the display is configured to display to the user a suggested or programmed maximum tracking rate (MTR) or interval value, a minimum AV delay value, a maximum AV delay value, a sensed AV offset value, a minimum post ventricular atrial refractory period (PVARP) value, a maximum PVARP value, and an AV search hysteresis value.

Example 32 describes a method comprising displaying to a user a graphical indication of AV interval vs. heart rate or interval. The method also comprises displaying to the user at least one of: first data of predicted or measured intrinsic conducted AV interval as a function of heart rate or interval; second data of a time intervals, as a function of heart rate or interval, between a sensed atrial contraction and a sensed ventricular contraction occurring during the same cardiac cycle; and third data of time intervals, as a function of heart rate or interval, between a paced atrial contraction and a sensed ventricular contraction occurring during the same cardiac cycle. The method also comprises displaying to the user an indication of an expected or actual amount of ventricular pacing for at least one heart rate for at least one of the first data, the second data, and the third data.

Example 32 describes an apparatus comprising a user interface including a display configured to display to a user a graphical indication of AV interval vs. heart rate or interval and at least one of: first data of predicted or measured intrinsic conducted AV interval as a function of heart rate or interval; second data of a time intervals, as a function of heart rate or interval, between a sensed atrial contraction and a sensed ventricular contraction occurring during the same cardiac cycle; and third data of time intervals, as a function of heart rate or interval, between a paced atrial contraction and a sensed ventricular contraction occurring during the same cardiac cycle. The user interface is also configured to display to the user an indication of an expected or actual amount of ventricular pacing for at least one heart rate for at least one of the first data, the second data, and the third data.

This overview is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Certain cardiac function management devices can provide, among other things, needed pacing energy pulses to a subject to evoke responsive heart contractions. This can help sustain the subject's metabolic need for cardiac output when the subject's autonomic nervous system is unable to do so. However, delivering a pacing pulse to evoke a responsive heart contraction when the subject's heart chamber would have contracted shortly thereafter anyway can, over a period of time, be deleterious. This is because excessive unnecessary ventricular pacing can advance the progression of congestive heart failure. Therefore, decreasing or minimizing unnecessary ventricular pacing can be helpful in avoiding such advancement of heart failure disease progression.

Figure 1:
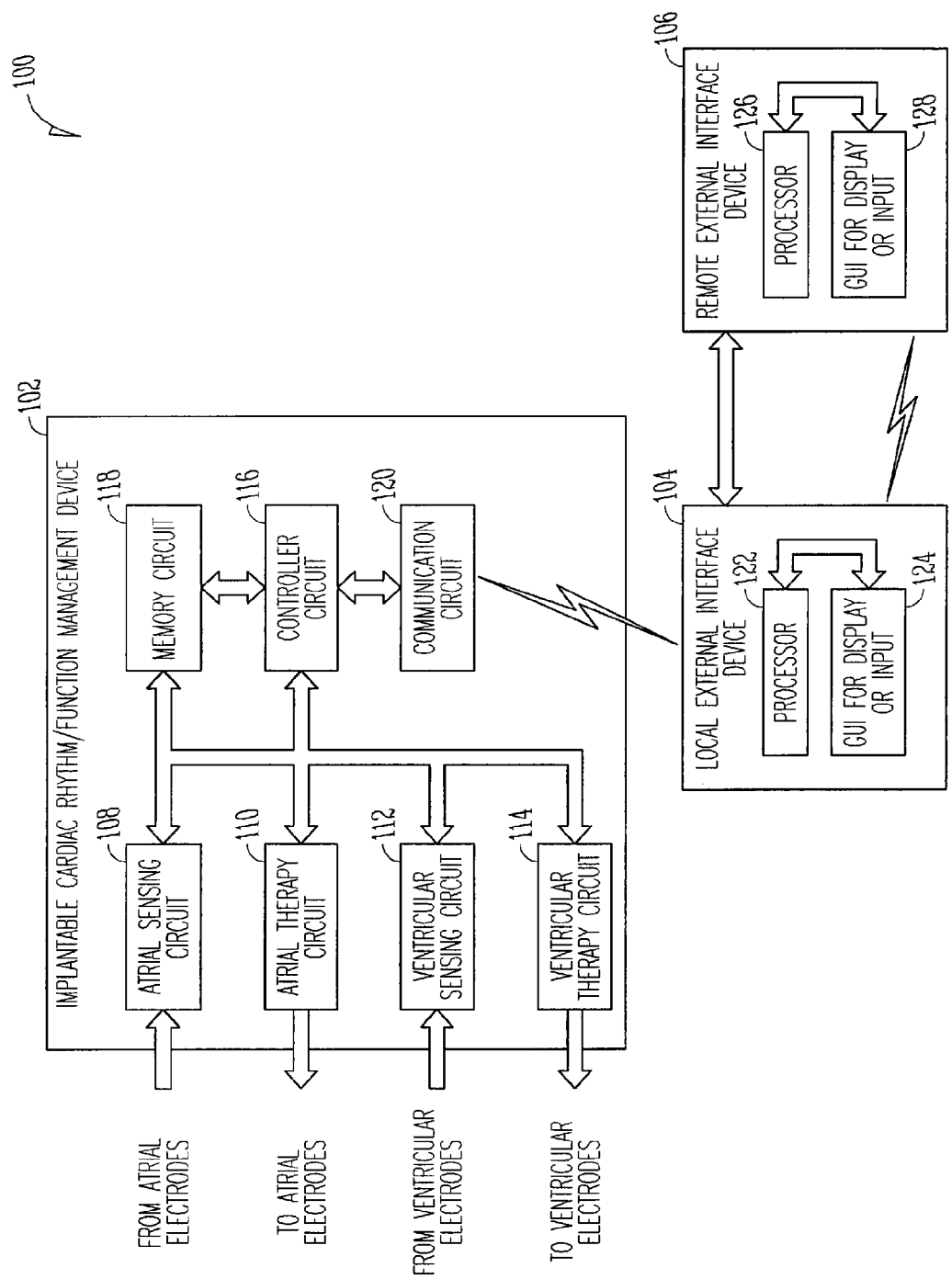
FIG. 1 illustrates an example of portions of a cardiac function management system and an environment in which it is used.

FIG. 1 illustrates an example of portions of a cardiac function management system 100 and an environment in which it is used. In certain examples, the system 100 includes an implantable cardiac rhythm or function management device 102, a local external interface device 104, and an optional remote external interface device 106. In certain examples, the implantable device 102 includes an atrial sensing circuit 108, an atrial therapy circuit 110, a ventricular sensing circuit 112, a ventricular therapy circuit 114, a controller circuit 116, a memory circuit 118, and a communication circuit 120.

The atrial sensing circuit 108 is typically coupled to electrodes, such as an intra-atrial electrode or any other electrode that permits sensing of an intrinsic atrial cardiac signal including atrial depolarization information. The atrial therapy circuit 110 is typically similarly coupled to these or other electrodes for delivering pacing or other energy pulses to one or both atria. The ventricular sensing circuit 112 is typically coupled to electrodes, such as an intra-ventricular electrode or any other electrode that permits sensing of an intrinsic ventricular cardiac signal including ventricular depolarization information. The ventricular therapy circuit 114 is typically similarly coupled to these or other electrodes for delivering pacing or other energy pulses to one or both ventricles. A controller circuit 116 is coupled to the atrial sensing circuit 108 and the ventricular sensing circuit 112 to receive information from the sensed cardiac signals, and is coupled to the atrial therapy circuit 110 and the ventricular therapy circuit 114 to provide control or triggering signals to trigger timed delivery of the therapy pulses. A memory circuit 118 is coupled to the controller circuit 116, such as to store control parameter values, physiological data, or other information. A communication circuit 120 is coupled to the controller circuit 116 to permit radiofrequency (RF) or other wireless communication with an external device, such as the local external interface device 104 or the remote external interface device 106. The local external interface device 104 typically includes a processor 122 and a graphic user interface (GUI) 124 or like device for displaying information or receiving user input as well as a communication circuit, such as to permit wired or wireless communication with the remote external interface device 106 over a communications or computer network. Similarly, the remote external interface device 106 typically includes a processor 126 and a graphic user interface (GUI) 128 or like device for displaying information or receiving user input as well as a communication circuit, such as to permit wired or wireless communication with the local external interface device 104 over the communications or computer network. Because the system 100 includes processing capability in the implantable device 102 (e.g., provided by the controller circuit 116), the local external interface device 104 (e.g., provided by the processor 122), and the remote external interface device 106 (e.g., provided by the processor 126), various methods discussed in this document can be implemented at any of such locations, or tasks can be distributed between two or more of such locations.

As discussed above, excessive unnecessary ventricular pacing can advance the progression of congestive heart failure. Therefore, decreasing or minimizing unnecessary ventricular pacing can be helpful in avoiding such advancement of heart failure disease progression. Several control parameters of an implantable cardiac function management device can affect the amount of ventricular pacing that it provides. For example, a programmed atrioventricular (AV) delay interval defines a period of time initiated by sensing an atrial contraction or delivering an atrial pacing pulse. If no ventricular contraction is sensed during the programmed AV delay interval, or a specified portion thereof, then a ventricular pacing pulse is delivered upon expiration of the programmed AV delay interval.

Moreover, the AV delay also typically is used as an atrial refractory period, during which time any detected atrial depolarization candidates are ignored as being noise, since under normal heart rhythm circumstances, no further atrial contractions are expected until after a ventricular contraction has been sensed or the AV delay has expired with the delivery of a ventricular pacing pulse. Even upon sensing a ventricular contraction or upon the expiry of the AV delay with the delivery of a ventricular pacing pulse, a post ventricular atrial refractory period (PVARP) is initiated. During the PVARP, any detected atrial depolarization candidates are still ignored as being noise, since under normal heart rhythm circumstances, no further atrial contractions are expected during the PVARP. The PVARP also prevents retrograde conduction of the ventricular depolarization or pacing pulse (traveling from the ventricle back toward the atrium) from erroneously being detected as another atrial contraction. The sum of the AV delay interval and the PVARP can be referred to as the total atrial refractory period (TARP), during which time candidate atrial depolarization detections are ignored as noise.

Although a simple fixed programmed AV delay interval could be used, in practice, more complex variations of the programmed AV delay interval can be implemented. For example, a programmed AV delay that is initiated by sensed atrial contractions (A-sense initiated AV delay) can be specified to be different than a programmed AV delay that is initiated by paced atrial contractions (A-pace initiated AV delay). The A-sense initiated AV delay is typically longer than an A-pace initiated AV delay, such as by an amount of time that can be referred to as a sensed AV-offset. The sensed AV-offset can represent an additional incremental amount of time for detecting a P-wave, indicative of an atrial contraction, from a sensed atrial cardiac signal. In this way, the A-sense initiated AV delay would effectively expire at the same time as the A-pace initiated AV delay, since the A-sense initiated AV delay is adjusted (slightly increased) by the sensed AV-offset.

Moreover, the A-sense initiated AV delay and the A-pace initiated AV delay can each be made dynamic, for example, by providing an automatic shortening of such AV delays (e.g., from their resting values) at higher heart rates (such as during strenuous exercise). Such a dynamic AV delay is particularly useful at high heart rates, such as heart rates that approach an upper rate limit (URL) of the implantable cardiac function management device, because the resting AV delay value may be inappropriately long at heart rates that are at or near the URL. Certain techniques of establishing a dynamic AV delay allows a clinician to specify a programmable value of a minimum AV delay (Min AV Delay) parameter, which can serve to limit how far the dynamic AV delay interval can be shortened at high heart rates (e.g., during strenuous exercise). The clinician can also be permitted to specify a programmable value of a maximum AV delay (Max AV Delay) parameter, which provides an upper bound for the dynamic AV delay interval at low heart rates (e.g., at rest).

In a similar manner, the PVARP can also be made dynamic, for example, by providing an automatic shortening of the PVARP (e.g., from its resting value) at higher heart rates (such as during strenuous exercise). Such a dynamic PVARP is particularly useful at high heart rates, such as heart rates that approach the URL, because the resting PVARP may be so long as to inappropriately inhibit sensing of an actual subsequent atrial contraction that initiates the next cardiac cycle. Certain techniques of establishing a dynamic PVARP allows a clinician to specify a programmable value of a minimum PVARP (Min PVARP) parameter, which can serve to limit how far the dynamic PVARP interval can be shortened at high heart rates (e.g., during strenuous exercise). The clinician can also be permitted to specify a programmable value of a maximum PVARP (Max PVARP) parameter, which provides an upper bound for the dynamic PVARP at low heart rates (e.g., at rest).

In certain examples, one or more control parameters permit different URLs to be established. For example, a maximum tracking rate (MTR) is a clinician-programmable parameter having a value that determines a URL that limits how fast the cardiac function management device can pace a ventricle in response to sensed intrinsic atrial contractions. Even if the rate of sensed intrinsic atrial contractions exceeds the MTR, the rate of ventricular pacing pulses being provided will be limited by the MTR. As another example, a maximum sensor rate (MSR) is a clinician-programmable parameter having a value that determines a URL that limits how fast the cardiac function management device can pace in response to a physiologic sensor indicating a metabolic need for cardiac output. An example of such a physiologic sensor includes an accelerometer that is configured to provide information about patient activity, such that strenuous exercise indicates a greater metabolic need for cardiac output. Another example of such a physiologic sensor includes a thoracic impedance sensor that is configured to provide information about patient breathing, such that rapid breathing indicates a greater metabolic need for cardiac output than does slower breathing. Other sensors or blended sensors are also possible. In any case, after the physiologic sensor drives the pacing rate up to the MSR, further increases in metabolic need indicated by the physiologic sensor do not result in further increases in pacing rate beyond the MSR.

To reduce or avoid unnecessary ventricular pacing, an AV search hysteresis (AVSH) can be used. The AVSH occasionally extends the AV delay by a specified AVSH percentage or other amount to see whether doing so will allow a ventricular contraction to be sensed during the AVSH extension of the AV delay interval. This is useful, for example, when there exists an underlying intrinsically conducted AV depolarization waveform that takes slightly longer than the AV delay interval. By occasionally extending the AV delay interval by the AVSH extension time, this allows the device to discover such underlying intrinsic ventricular contractions. If such underlying ventricular contractions are so discovered, then the AV delay interval can be automatically adjusted to allow the underlying intrinsic ventricular rhythm to take over. This avoids unnecessary ventricular pacing and, therefore, will help avoid contributing to advancement of the subject's heart failure disease progression.

At high heart rates, such as at or near the URL imposed by the MSR or MTR, certain undesirable effects can occur if certain control parameters are not programmed properly. As discussed above, an inappropriately long value of PVARP could result in an actual atrial depolarization being ignored as noise since it falls within the PVARP. Since AVSH extends the AV delay interval, it also extends the TARP, which could similarly result in an actual atrial depolarization being ignored as noise since the extended AV delay and TARP could cause such actual atrial depolarization to fall within the TARP. Programming AVSH can be complicated because of its interactions with AV delay, MTR, MSR, and PVARP.

Because of the complex interrelationships between control parameters, such as those described above, it is difficult to expect clinicians to properly program the implantable cardiac function management device to provide the desired operating behavior at both low and high heart rates—particularly where the clinician is also interested in avoiding unnecessary ventricular pacing so as to help avoid contributing to advancement of the subject's heart failure disease progression.

The present inventor has observed, among other things, that the AV delay interval and AVSH percentage needed to avoid unnecessary ventricular pacing are often overestimated by clinicians. However, such programming to avoid unnecessary ventricular pacing can result in poor hemodynamics if ventricular pacing is ever needed by the subject. Moreover, one or more other parameters (e.g., MSR) may be compromised by the clinician in order to maintain an unnecessarily inflated AV delay and AVSH percentage that the clinician thinks is needed to avoid unnecessary ventricular pacing.

Figure 2:
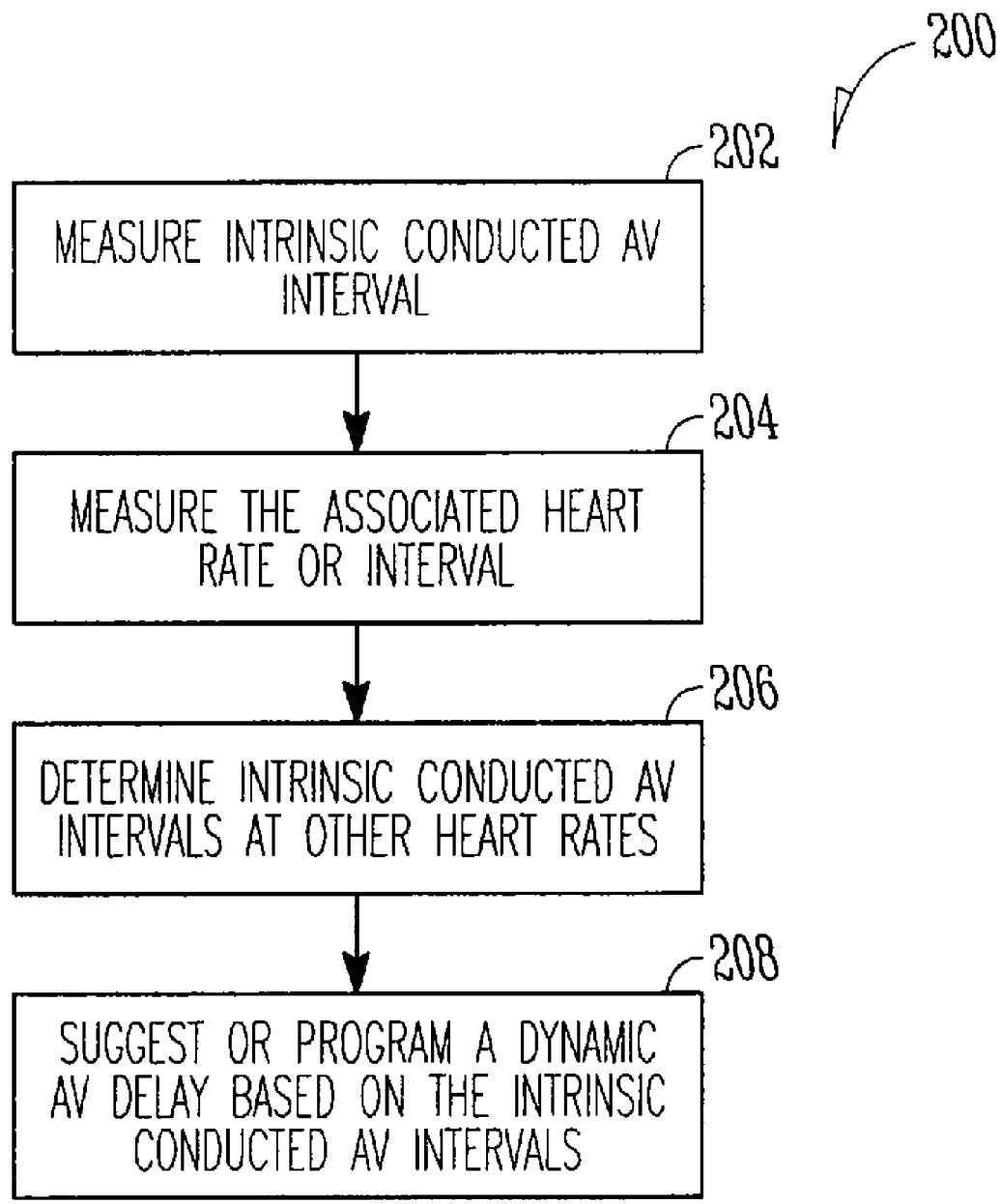
FIG. 2 illustrates an example of a method that helps establish a dynamic atrioventricular (AV) delay at a hemodynamically beneficial value that generally avoids unnecessary ventricular pacing that might contribute to the advancement of the subject's heart failure disease progression.

FIG. 2 illustrates an example of a method 200 that helps establish a dynamic AV delay at a hemodynamically beneficial value that generally avoids unnecessary ventricular pacing that might contribute to the advancement of the subject's heart failure disease progression. At 202, an intrinsic conducted AV interval is measured, such as by using a time from an atrial pacing pulse (e.g., issued by the atrial therapy circuit 110) to a subsequent sensed ventricular contraction (e.g., detected by the ventricular sensing circuit 112) during the same cardiac cycle, or by using a time from a sensed atrial contraction (e.g., detected by the atrial sensing circuit 108) to a subsequent sensed ventricular contraction (e.g., detected by the ventricular sensing circuit 112) during the same cardiac cycle. At 204, a heart rate or interval associated with the intrinsic conducted AV interval measured in 202 is measured and stored in association with the information about the intrinsic conducted AV interval. This can include measuring an interval between successive P-waves or other indications of successive atrial contractions, or measuring an interval between successive R-waves or other indications of successive ventricular contractions, or a combination of such two measurements.

At 206, intrinsic conducted AV intervals are determined at other heart rates. This can be accomplished in a number of different ways. For example, for a newly implanted device 102, for which no stored data is yet available about the intrinsic conducted AV intervals and their associated heart rates or intervals, this can include extrapolating such data from the intrinsic conducted AV interval measured at 202 and its associated heart rate or interval measured at 204, as discussed further below. For a device that has been implanted in a subject for a time period suitable to obtain and store, in normal operation, measurements of intrinsic conducted AV intervals over a range of heart rates, such actual measured data of intrinsic conducted AV intervals and associated heart rates or intervals can be used instead of or in combination with such extrapolation.

At 208, a dynamic AV delay is automatically suggested to the clinician or automatically programmed based on the extrapolated or measured intrinsic conducted AV intervals and associated heart rates of 206.

Figure 3:
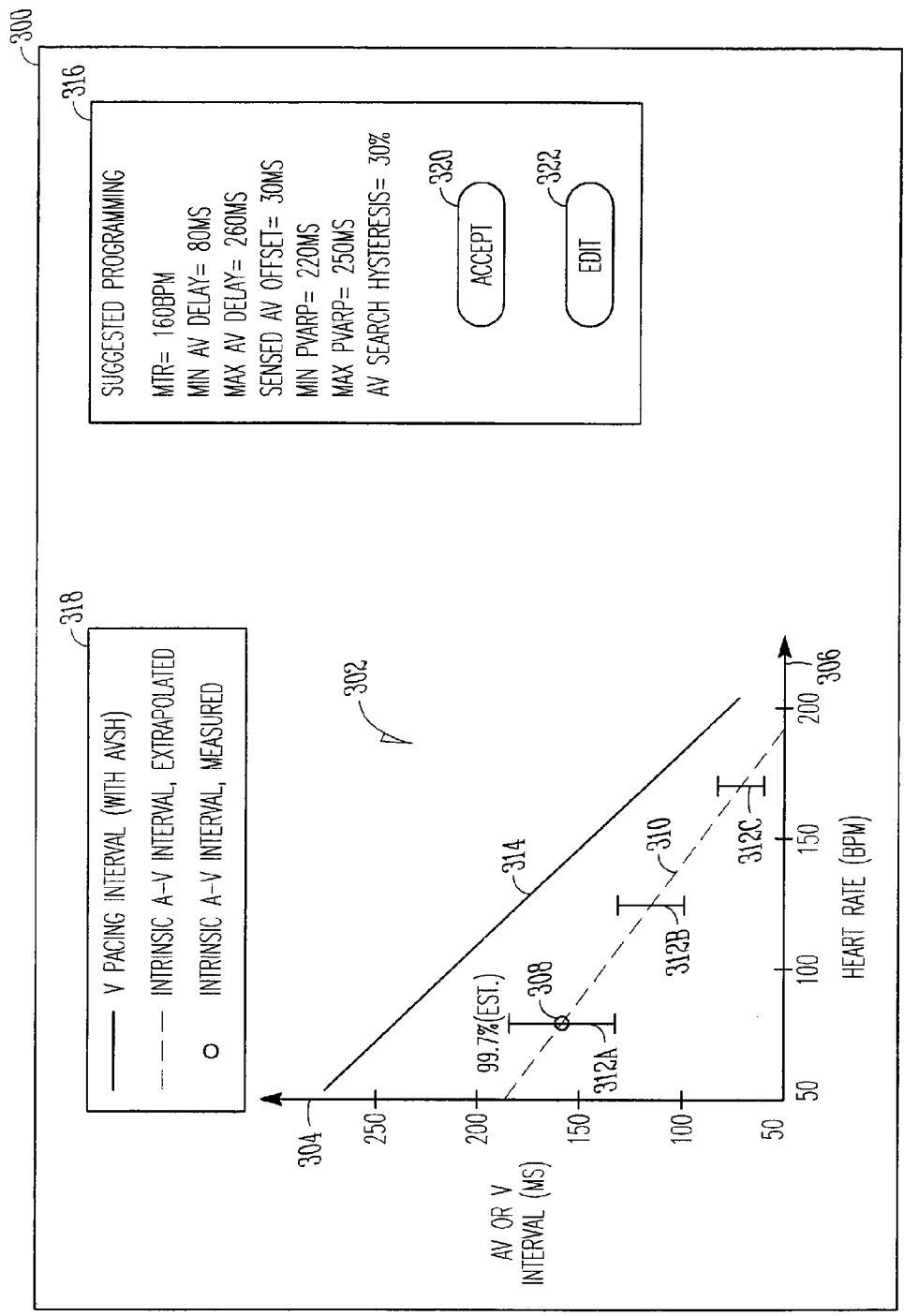
FIG. 3 illustrates a useful at least partially graphical technique of suggesting the dynamic AV delay to the clinician, such as by displaying such information on a display of a graphical user interface (GUI).

FIG. 3 illustrates a useful at least partially graphical technique of suggesting the dynamic AV delay to the clinician, such as by displaying such information on a display 300 of a GUI 124 or 128. In the example of FIG. 3, the display 300 includes a graph 302 of AV or V interval (milliseconds) 304 vs. heart rate (beats per minute) 306. In this example, the graph 302 illustrates a single measured value 308 of the intrinsic conducted AV interval (e.g., as measured at 202) at its associated heart rate (e.g., as measured at 204). In this example, extrapolated values of intrinsic conducted AV interval at various different heart rates are displayed as (linear or nonlinear) function 310, together with optional confidence bars 312 indicating a computed statistical confidence in the data presented by the conducted AV interval function 310. While the example shown in FIG. 3 displays an extrapolated function 310 that is extrapolated from the measured value 308, as can be displayed at implantation of the cardiac device 102 when there is no measured data available across the various heart rates, in other examples in which the cardiac device 102 has been implanted for a period of time, such measured data can be displayed instead of or in addition to the extrapolated function 310.

In the example of FIG. 3, the displayed graph 302 also includes a (linear or nonlinear) function 314 indicating the ventricular pacing interval that will be provided by the implanted cardiac device 102, given a suggested set of programming parameters 316. In certain examples, the particular set of programming parameters 316 is automatically computed so as to provide a desired safety margin by which the ventricular pacing interval function 314 will be longer than the predicted or actual intrinsic conducted AV interval function 310 at each of the various heart rates or intervals. In certain examples, the particular set of programming parameters 316 is suggested such that the safety margin is between about 3% and about 200% of the intrinsic conducted AV interval for at least one of the different heart rates or intervals, or for all of the different heart rates or intervals. In certain examples, the particular set of programming parameters 316 is suggested such that the safety margin is between about 5% and about 20% of the intrinsic conducted AV interval for at least one of the different heart rates or intervals, or for all of the different heart rates or intervals. In certain examples, the particular set of programming parameters 316 is suggested such that the safety margin is between about 10 milliseconds and about 100 milliseconds for at least one of the different heart rates or intervals, or for all of the different heart rates or intervals. In certain examples, the particular set of programming parameters 316 is suggested such that the safety margin is between about 10 milliseconds and about 100 milliseconds for at least one of the different heart rates or intervals, or for all of the different heart rates or intervals.

In this example, the displayed ventricular pacing interval function 314 accounts for a suggested AVSH percentage. The displayed graph 302 makes it easy for the clinician to see whether the ventricular pacing interval function 314 that will be obtained by the implanted cardiac device 102 using the suggested set of programming parameters 316 will adequately exceed the conducted AV interval function 310— e.g., including the displayed confidence bars 312—across the various heart rates. In this manner, a clinician need not program an unnecessarily inflated AV delay and AVSH percentage that the clinician thinks is needed to avoid unnecessary ventricular pacing. This results in more hemodynamically beneficial programmed values of one or more control parameters such as AV delay and AVSH percentage while still avoiding unnecessary ventricular pacing.

The example of FIG. 3 also illustrates an example of a displayed legend 318 accompanying the displayed graph 302, such as to assist the clinician in interpreting the displayed graph 302. An automatically computed set of suggested programming parameters 316 is also displayed, which in this example includes values for MTR, Min AV Delay, Max AV Delay, Sensed AV Offset, Min PVARP, Max PVARP, and AV Search Hysteresis percentage. If the clinician is satisfied with the displayed V pacing interval function 314 obtained by the displayed suggested programming parameters 316, the clinician can select the displayed "Accept" button 320, which accepts and programs the implanted cardiac device 102 with the displayed values of the suggested programming parameters 316, otherwise, the clinician can select the displayed "Edit" button 322, to edit one or more values of the displayed suggested programming parameters 316. In response to such clinician editing of the values of the displayed suggested programming parameters, the display 300 re-displays a new V pacing interval function 314 that is automatically recomputed using any such clinician-edited parameter values.

Figure 4:
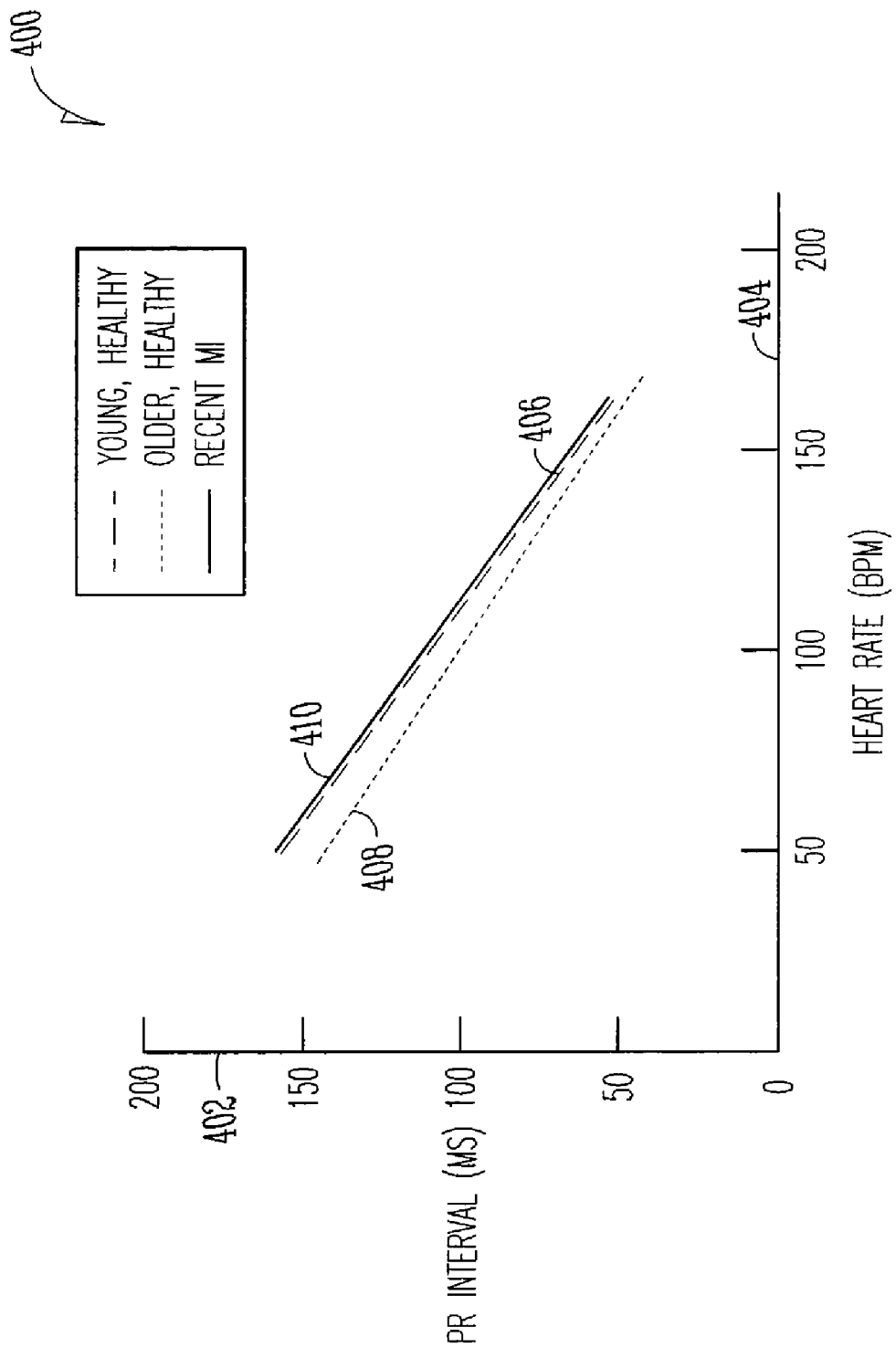
FIG. 4 is a graph of intrinsic conducted AV interval (e.g., PR interval between an intrinsic cardiac signal's P-wave indicating an atrial contraction and its R-wave indicating a ventricular contraction) in milliseconds vs. heart rate in beats per minute, which illustrates an example of how one or more measured values of intrinsic conducted AV interval at a corresponding heart rate can be used to extrapolate to other predicted values of intrinsic conducted AV interval at other heart rates.

FIG. 4 is a graph 400 of intrinsic conducted AV interval 402 (e.g., PR interval between an intrinsic cardiac signal's P-wave indicating an atrial contraction and its R-wave indicating a ventricular contraction) in milliseconds vs. heart rate 404 in beats per minute, which illustrates an example of how one or more measured values of intrinsic conducted AV interval at a corresponding heart rate can be used to extrapolate to other predicted values of intrinsic conducted AV interval at other heart rates. FIG. 4 illustrates a first intrinsic conducted AV interval function 406 across various heart rates for one or more young and healthy subjects, a second intrinsic conducted AV interval function 408 across various heart rates for one or more older and healthy subjects, and a third intrinsic conducted AV interval function 410 across various heart rates for one or more subjects who have experienced a recent myocardial infarction. In certain examples, published or other clinical data from such patients or patient populations would be obtained, and such functions would be fitted thereto. Other patient populations could also be identified and used to provide separate functions, such as by using a patient's age, health status, or the like. A composite function can be obtained to aggregate data from more than one or all such patients or patient populations. The graph of FIG. 4 may—but need not—be displayed to the clinician.

As an illustrative example, extrapolating from a single measured value of the subject's intrinsic conducted AV interval (e.g., measured at 202) and its corresponding heart rate or interval (e.g., measured at 204) can be performed by selecting a particular one of the functions 406, 408, 410, and translating that function to overlie the subject's single measured value of intrinsic conducted AV interval at the corresponding heart rate or interval. The translated function can then be used as an extrapolation of the single measured value of the subject's intrinsic conducted AV interval, such as to provide predicted values of the intrinsic conducted AV interval at other heart rates, which can be displayed at 310. If more than one measured value of the intrinsic conducted AV interval is available, a curve-fitting technique can be used to best fit a selected one of the functions 406, 408, and 410 to the measured values of the intrinsic conducted AV interval, and the fitted function can be used to provide predicted values of the intrinsic conducted AV interval at other heart rates, which can be displayed at 310. If enough measured values of the particular subject's intrinsic conducted AV interval at various heart rates are available for use (such as where the cardiac device 102 has been implanted in a subject for a long enough period of time to allow data collection over a range of heart rates), then such measured values can be used instead of published or other clinical patient or population data. For example, curve-fitting can be used to generate a best-fit subject-specific function, which can be displayed at 310.

In the example of FIG. 3, automatically computing the suggested programming parameters 316 can involve various techniques. For example, a URL parameter, such as MSR or MTR, can be automatically determined using information about the particular subject in which the cardiac device 102 is implanted, such as in combination with other information obtained from published or other clinical data from one or more other patients or populations of patients. As an example, using information about the subject's age, the controller circuit 116 can use a look-up table stored in the memory circuit 118 to compute an age-predicted maximum heart rate, and the suggested URL parameter, such as MSR or MTR can be automatically established to be at a specified safety margin (e.g., 10 bpm) below the age-predicted maximum heart rate (or above the age-predicted maximum heart rate interval). In certain examples, the URL parameter, such as MSR or MTR, is specified by the clinician as user-input, and the other suggested programming parameters 316 are determined using such user-specified value of at least one URL parameter.

Figure 5:
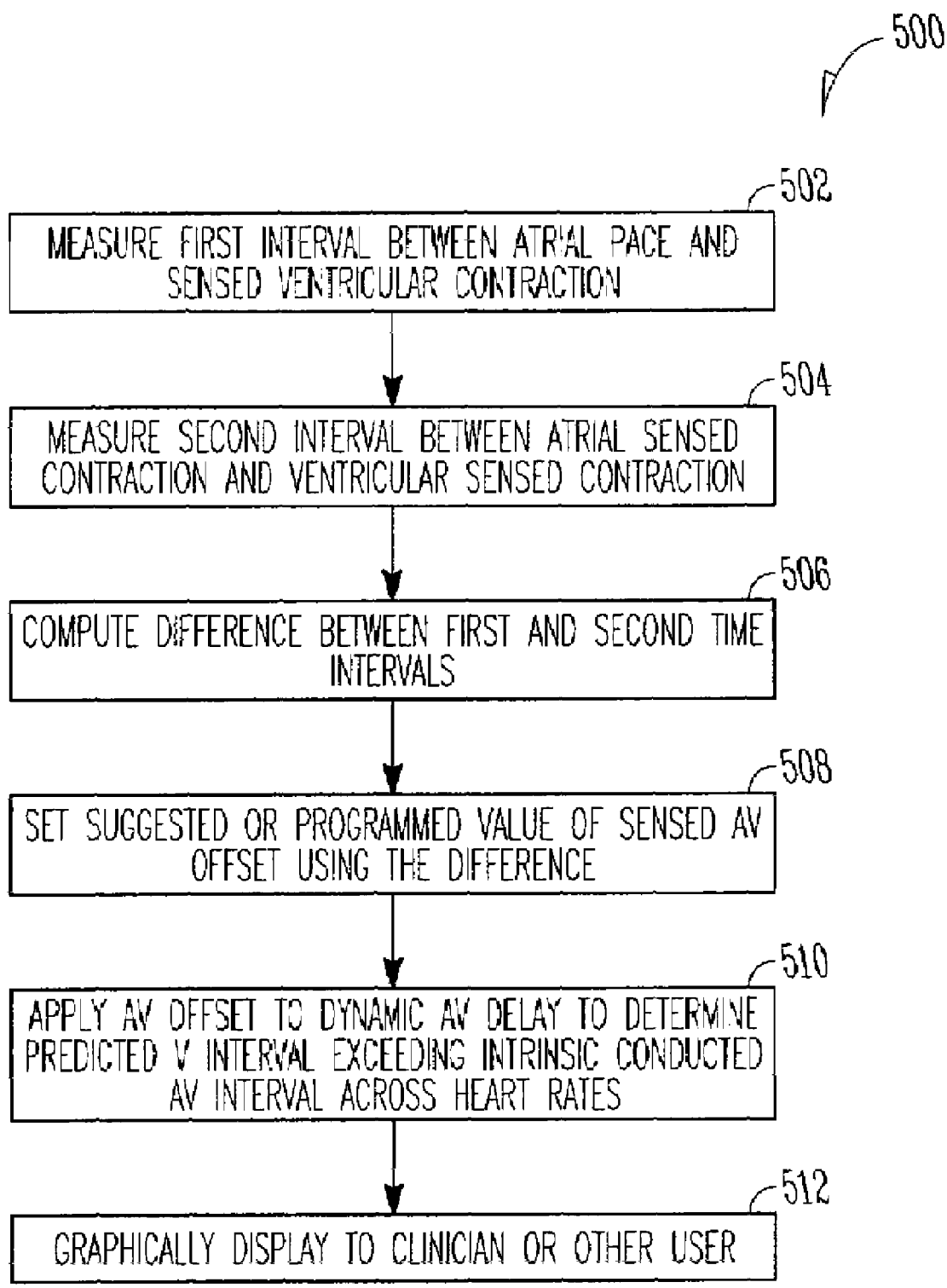
FIG. 5 illustrates generally an example of a technique of automatically determining a physiologically appropriate sensed AV offset value.

FIG. 5 illustrates generally an example of a technique 500 of automatically determining a physiologically appropriate sensed AV offset value. In this example, at 502, a first time interval is measured between an atrial pace and a subsequent sensed ventricular contraction occurring during the same cardiac cycle. This measurement can be performed by a timer in the controller circuit 116, such as by using information about timing of an atrial pace triggering control signal provided by the controller circuit 116 to the atrial therapy circuit 110 and information about timing of a sensed ventricular contraction received by the controller circuit 116 from the ventricular sensing circuit 112.

At 504, a second time interval is measured between a sensed atrial contraction and a subsequent sensed ventricular contraction occurring during the same cardiac cycle. This measurement can be performed by a timer in the controller circuit 116, such as by using information about timing of a sensed atrial contraction provided by the atrial sensing circuit 108 to the controller circuit 116 and information about timing of a sensed ventricular contraction received by the controller circuit 116 from the ventricular sensing circuit 112.

At 506, a difference between the first and second time intervals is computed. This difference calculation can be performed by the controller circuit 116. At 508, the difference between the first and second time intervals can be used to automatically suggest or program a sensed AV offset value, such as by setting the suggested or programmed sensed AV offset value equal to the value of the computed difference between the first and second time intervals.

At 510, the suggested AV offset value is applied to the dynamic AV delay as a part of arriving at the suggested programming parameters 316 that provide a resulting ventricular pacing interval function 314 that will exceed the measured or predicted conducted intrinsic AV interval 310 across the various heart rates, such as by any user or device specified safety margin.

At 512, information is displayed to the clinician or other user, such as in an at least partially graphical display of the resulting ventricular pacing interval function 314 together with information about the suggested sensed AV offset value and values of the other programming parameters 316, such as illustrated in the example of FIG. 3.

Figure 6:
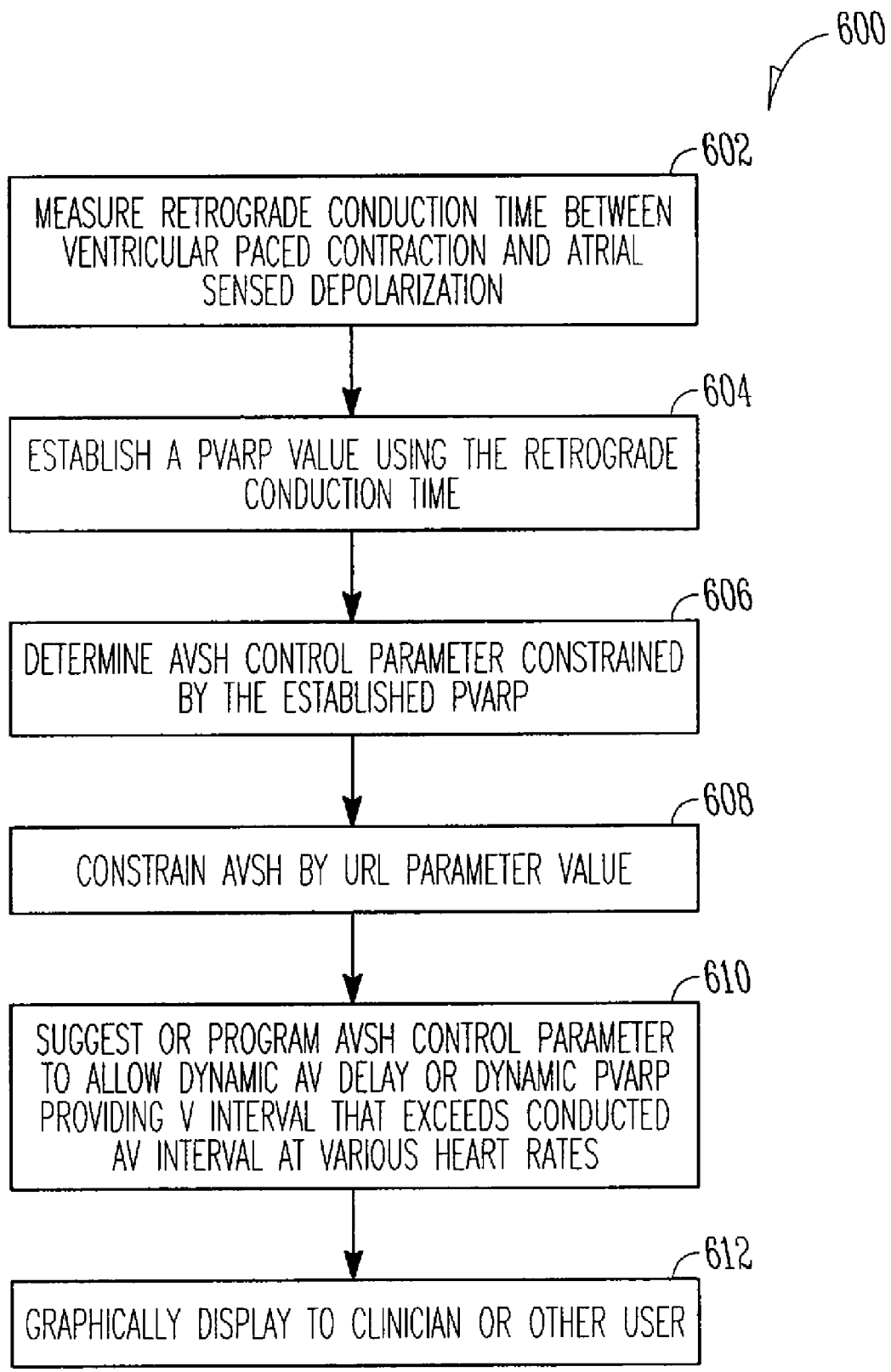
FIG. 6 illustrates generally an example of a technique of automatically determining a PVARP, which can then be optionally used to constrain the suggested value of the AVSH control parameter, which can also be constrained using a URL parameter.

FIG. 6 illustrates generally an example of a technique 600 of automatically determining a PVARP, which can then be optionally used to constrain the suggested value of the AVSH control parameter, which can also be constrained using a URL parameter. In this example, at 602, a retrograde conduction time is measured between a ventricular paced contraction and a resulting sensed atrial depolarization. The time of the ventricular paced contraction can be determined by the timing of a ventricular pace triggering signal provided by the controller circuit 116 to the ventricular therapy circuit 114. The timing of the resulting sensed atrial depolarization can be determined by information provided by the atrial sensing circuit 108 (e.g., with any atrial sensing refractory disabled during such sensing so as to permit detection of the atrial sensed depolarization resulting from the ventricular pace).

At 604, a PVARP value is determined, such as by using the retrograde conduction time measured in 602. In certain examples, this includes ensuring that the dynamic PVARP always exceeds the retrograde conduction time (plus any desired specified safety margin), such as by suggesting or programming the minimum PVARP and maximum PVARP to exceed such value. Suggested minimum and maximum PVARP values can be displayed to the user, such as shown in the example of FIG. 3.

At 606, an AVSH control parameter value is established, such as for being displayed as a suggested value to a clinician, or for being automatically programmed. In certain examples, the AVSH control parameter value is constrained by the PVARP values determined at 604. As discussed above, the AVSH control parameter controls providing an occasionally extended dynamic AV delay to allow an additional time period for ventricular sensing. In certain examples, the AVSH is constrained such that the resulting extended dynamic AV delay interval is always longer than a sum of a minimum value of the dynamic AV delay interval (e.g., min AV delay) and a minimum value of the dynamic PVARP (e.g., min PVARP).

At 608, the AVSH control parameter value can also be additionally constrained by a URL parameter value, such as an MTR or MSR value. The URL parameter value can be determined, for example, using an age-predicted URL or like technique, as discussed above. The AVSH control parameter can be constrained by the URL parameter value such that the resulting extended dynamic AV delay interval is always shorter than an upper rate limit (URL) interval.

At 610, the resulting AVSH control parameter (e.g., constrained by the PVARP, URL, or any other constraints) can be displayed or otherwise suggested to the user (e.g., as shown in the example of FIG. 3), or automatically programmed into the cardiac device 102. The resulting AVSH control parameter is computed such that any resulting ventricular interval exceeds the conducted AV interval across the various heart rates, as discussed above with respect to FIG. 3. At 612, such information can be conveyed to the user, such as illustrated above with respect to FIG. 3.

Figure 7:
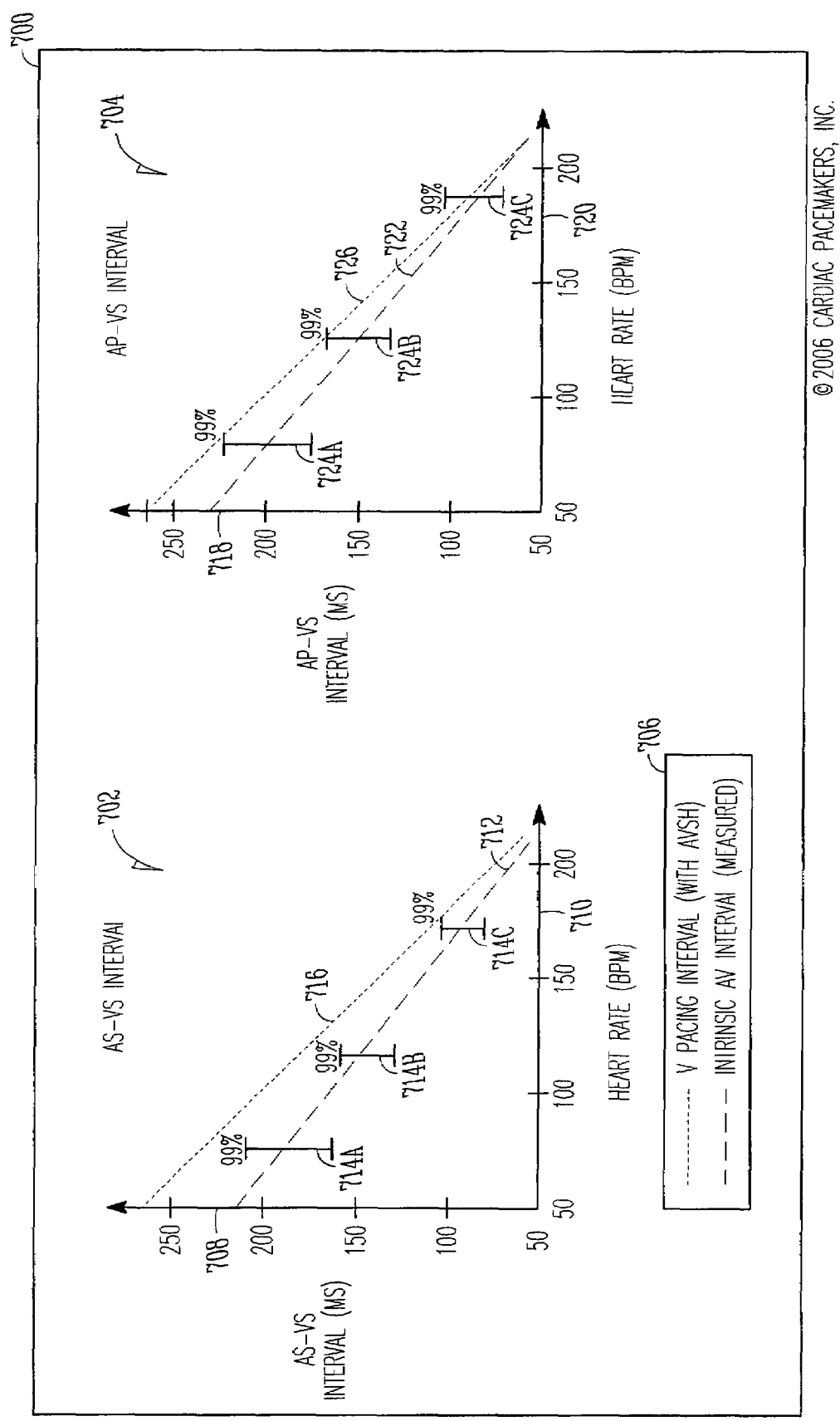
FIG. 7 illustrates another useful at least partially graphical technique of providing useful information to the clinician, such as to allow the clinician to visualize how much ventricular pacing is occurring as a result of a given set of programmed control parameter values.

FIG. 7 illustrates another useful at least partially graphical technique of providing useful information to the clinician, such as to allow the clinician to visualize how much ventricular pacing is occurring as a result of a given set of programmed control parameter values. The information illustrated in FIG. 7 can be provided on a display 700, such as of a GUI 124 or 128. In the example of FIG. 7, the display 700 includes a first graph 702 of AV intervals initiated by a sensed atrial contraction, a second graph 704 of AV intervals initiated by a paced atrial contraction, and a legend 706.

In this example, the first graph 702 includes a y-axis 708 representing AV intervals initiated by sensed atrial events (e.g., AS-VS Intervals), in milliseconds, and an x-axis 710 representing heart rate, in beats per minute. A displayed function 712 illustrates an intrinsic conducted AV interval. In certain examples, this includes historical measured data of intrinsic conducted AV interval and corresponding heart rates obtained from the subject with the implanted device 102. Such historical data can be fitted to a line or other function to plot as the displayed function 712, together with confidence interval bars 714. In the illustrated example, the confidence interval bars 714 represent 99% confidence intervals, or other user or device specified confidence values, as desired. The displayed function 716 represents, across various heart rates, the ventricular interval value obtained with a particular set of control parameter values (such as the suggested control parameter values, e.g., determined as described above, or the current parameter values in effect over the period of time for which the historical intrinsic conducted AV interval data was acquired, or a user-specified set of control parameters).

In this example, the second graph 704 includes a y-axis 718 representing AV intervals initiated by paced atrial events (e.g., AP-VS Intervals), in milliseconds, and an x-axis 720 representing heart rate, in beats per minute. A displayed function 722 illustrates an intrinsic conducted AV interval. In certain examples, this includes historical measured data of intrinsic conducted AV interval and corresponding heart rates obtained from the subject with the implanted device 102. Such historical data can be fitted to a line or other function to plot as the displayed function 722, together with confidence interval bars 724. In the illustrated example, the confidence interval bars 724 represent 99% confidence intervals, or other user or device specified confidence values, as desired. The displayed function 726 represents, across various heart rates, the ventricular interval value obtained with a particular set of control parameter values (such as the suggested control parameter values, e.g., determined as described above, or the current parameter values in effect over the period of time for which the historical intrinsic conducted AV interval data was acquired, or a user-specified set of control parameters).

In the example of FIG. 7, it is easy for the clinician to see that some ventricular pacing will occur at high heart rates for AV intervals that are initiated by paced atrial contractions. This allows the clinician to adjust the programmed value of the sensed AV offset, or any other desired control parameter value, such as to avoid such ventricular pacing observed at higher heart rates in graph 704. In the example of FIG. 7, if enough measured intrinsic conducted AV interval data is unavailable (such as at implant), predicted values can be used instead, such as by using the single measurement and extrapolation techniques described above.

In the examples of FIGS. 3 and 7, the displayed ventricular pacing interval functions 314, 716, and 726 were discussed emphasizing an example in which such functions resulted from an automatically computed set of suggested programming parameter values, such as the suggested programming parameter values 316. One technique to modify the resulting ventricular pacing interval function was to allow the user to select the edit button 322, which would permit the user to edit the suggested programming parameter values 316 to be different from those automatically computed and suggested by the device. In another example, the user can use a mouse-cursor to "drag-and-drop" a selected one of the displayed ventricular pacing interval function to a different location, such as to obtain more or less safety margin to avoid unnecessary ventricular pacing, for example. In certain such examples, the controller circuit 116 automatically re-computes a new set of suggested programming parameter values 316 to provide the user-dragged-and-dropped ventricular pacing interval 314.

In any of the above examples, processing described as being carried out by a particular one of the controller circuit 116, local external interface device processor 122, and remote external interface device processor 126 can be carried out in whole or in part by another one or more of such elements. In many situations, it is desirable to communicate data from the implantable cardiac device 102 to one or the local external interface device 104 or the remote external interface device 106, such as to harness the processing power thereof, or to access historical data from the subject or from a population of other patients.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description.

The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A method of programming an implantable cardiac rhythm management device to avoid unnecessary ventricular pacing, the method comprising:

measuring an intrinsic conducted AV interval at a first heart rate or interval, wherein the intrinsic conducted AV interval is initiated by either a sensed or paced atrial contraction and is concluded by a sensed ventricular contraction;

measuring the first heart rate or interval;

automatically measuring or automatically extrapolating intrinsic conducted AV intervals at heart rates or intervals that are different from the first heart rate or interval to determine a measured or predicted intrinsic conducted AV interval as a function of different heart rates or intervals, wherein the automatically extrapolating includes using the measured intrinsic conducted AV interval at the measured first heart rate or interval and the measured first heart rate or interval for performing the extrapolating; and automatically suggesting or automatically programming a dynamic AV delay interval, based upon the measured or predicted intrinsic conducted AV interval as a function of the different heart rates or intervals, such that the dynamic AV delay interval is longer than the measured or predicted intrinsic conducted AV interval at each of the different heart rates or intervals, wherein automatically suggesting or automatically programming the dynamic AV delay interval to be longer than the measured or predicted intrinsic conducted AV interval at each of the different heart rates or intervals includes:

determining a sensed AV offset using a difference between (1) a first time interval between an atrial paced contraction and a ventricular sensed contraction during at least one first cardiac cycle and (2) a second time interval between an atrial sensed contraction and a ventricular sensed contraction during at least one second cardiac cycle; and applying the determined sensed AV offset to the dynamic AV delay interval to obtain an AV-offset adjusted dynamic AV delay interval that is longer than the measured or predicted intrinsic conducted AV interval at each of the different heart rates or intervals.

2. The method of claim 1, in which automatically extrapolating the predicted intrinsic conducted AV interval as a function of different heart rates or intervals includes using a patient's age in performing the extrapolating.

3. The method of claim 1, in which automatically extrapolating the predicted intrinsic conducted AV interval as a function of different heart rates or intervals includes using information about the patient's health status in performing the extrapolating.

4. The method of claim 3, in which automatically extrapolating the predicted intrinsic conducted AV interval as a function of different heart rates or intervals includes using information about a recent myocardial infarction in performing the extrapolating.

5. The method of claim 1, in which automatically suggesting or automatically programming a dynamic AV delay includes providing a safety margin by at least which the dynamic AV delay is longer than the measured or predicted conducted AV interval at each of the different heart rates or intervals.

6. The method of claim 1, comprising automatically suggesting or automatically programming an upper rate limit (URL) parameter using an age-predicted maximum heart rate or interval based on information about at least one of a patient's age or activity level, wherein the UIRL parameter includes at least one of a maximum tracking rate (MRT) or interval or a maximum sensing rate (MSR) or interval.

7. The method of claim 1, comprising automatically suggesting, automatically programming, or automatically displaying the determined sensed AV offset that is applied to the determined sensed AV offset to the dynamic AV delay interval to obtain an AV-offset adjusted dynamic AV delay interval that is longer than the measured or predicted intrinsic conducted AV interval at each of the different heart rates or intervals.

8. The method of claim 1, comprising determining a dynamic post ventricular atrial refractory period (PVARP), including:

measuring a retrograde conduction time between a ventricular paced contraction and a sensed atrial depolarization; and establishing the dynamic PVARP to be greater than or equal to the measured retrograde conduction time, wherein the dynamic PVARP is used in determining the dynamic AV delay interval that is automatically suggested or automatically programmed to be longer than the measured or predicted intrinsic conducted AV interval at each of the different heart rates or intervals.

9. The method of claim 8, comprising automatically suggesting or programming the dynamic PVARP.

10. The method of claim 8, comprising determining an atrioventricular search hysteresis (AVSH) control parameter that controls providing an extended dynamic AV delay interval to allow an additional time period for ventricular sensing, including constraining the AVSH control parameter by selecting the AVSH control parameter to limit the extended dynamic AV delay interval to be longer than a sum of a minimum value of the dynamic AV delay interval and a minimum value of the dynamic PVARP.

11. The method of claim 10, wherein the constraining the AVSH control parameter comprises selecting the AVSH control parameter to limit the extended AV delay interval to be shorter than an upper rate limit (URL) interval.

12. The method of claim 10, comprising automatically suggesting or programming the AVSH control parameter.

13. The method of claim 10, comprising graphically displaying to a user the AVSH interval as a function of heart rate or interval, together with the measured or predicted intrinsic conducted AV interval as a function of heart rate or interval.

14. The method of claim 13, comprising graphically displaying to the user at least one of an indication of a safety margin by which the AVSH interval exceeds the measured or predicted intrinsic conducted AV interval or an indication of how much ventricular pacing is expected to occur.

15. The method of claim 1, comprising graphically displaying to a user an indication of the dynamic AV delay as a function of heart rate or interval, together with the measured or predicted intrinsic conducted AV interval as a function of heart rate or interval.

16. The method of claim 15, comprising graphically displaying to the user an indication of a safety margin by which the dynamic AV delay exceeds the measured or predicted intrinsic conducted AV interval or an indication of how much ventricular pacing is expected to occur.

17. The method of claim 1, comprising displaying to the user a suggested or programmed maximum tracking rate (MTR) or interval value, a minimum AV delay value, a maximum AV delay value, a sensed AV offset value, a minimum post ventricular atrial refractory period (PVARP) value, a maximum PVARP value, and an AV search hysteresis value.

18. The method of claim 1, comprising display of upper rate limit (URL) parameters, including at least one of a maximum tracking rate (MIRT) or interval or a maximum sensing rate (MSR) or interval, and the option to manually input the desired values for extrapolation of the dynamic AV Delay and/or AVSH value, a Sensed AV Offset value, a minimum and maximum PVARP, and predicted AV conduction interval as a function of different heart rates or interval.

19. An apparatus for programming an implantable cardiac rhythm management device to avoid unnecessary ventricular pacing, the apparatus comprising:
    means for measuring an intrinsic conducted AV interval at a first heart rate or interval, wherein the intrinsic conducted AV interval is initiated by either a sensed or paced atrial contraction and is concluded by a sensed ventricular contraction;
    means for measuring the first heart rate or interval;
    means for automatically measuring or automatically extrapolating intrinsic conducted AV intervals at heart rates or intervals that are different from the first heart rate or interval to determine a measured or predicted intrinsic conducted AV interval as a function of different heart rates or intervals, wherein the automatically extrapolating includes using the measured intrinsic conducted AV interval at the measured first heart rate or interval and the measured first heart rate or interval for performing the extrapolating; and
    means for automatically suggesting or automatically programming a dynamic AV delay interval, based upon the measured or predicted intrinsic conducted AV interval as a function of the different heart rates or intervals, such that the dynamic AV delay interval is longer than the measured or predicted intrinsic conducted AV interval at each of the different heart rates or intervals, wherein the means for automatically suggesting or automatically programming the dynamic AV delay interval to be longer than the measured or predicted intrinsic conducted AV interval at each of the different heart rates or intervals include:
        means for determining a sensed AV offset using a difference between (1) a first time interval between an atrial paced contraction and a ventricular sensed contraction during at least one first cardiac cycle and (2) a second time interval between an atrial sensed contraction and a ventricular sensed contraction during at least one second cardiac cycle; and
        means for applying the determined sensed AV offset to the dynamic AV delay interval to obtain an AV-offset adjusted dynamic AV delay interval that is longer than the measured or predicted intrinsic conducted AV interval at each of the different heart rates or intervals.

20. An apparatus for programming an implantable cardiac rhythm management device to avoid unnecessary ventricular pacing, the apparatus comprising:
    an atrial sensing circuit;
    an atrial therapy circuit;
    a ventricular sensing circuit;
    a ventricular therapy circuit;
    a controller circuit, coupled to the atrial sensing and therapy circuits and the ventricular sensing and therapy circuits, the controller circuit configured to:
    measure an intrinsic conducted AV interval at a first heart rate or interval, wherein the intrinsic conducted AV interval is initiated by either a sensed or paced atrial contraction and is concluded by a sensed ventricular contraction;
    measure the first heart rate or interval;
    measure or extrapolate intrinsic conducted AV intervals at heart rates or intervals that are different from the first heart rate or interval to determine a measured or predicted intrinsic conducted AV interval as a function of different heart rates or intervals, wherein the extrapolating includes using the measured intrinsic conducted AV interval at the measured first heart rate or interval and the measured first heart rate or interval for performing the extrapolating; and
    automatically suggest or automatically program a dynamic AV delay interval, based upon the measured or predicted intrinsic conducted AV interval as a function of the different heart rates or intervals, such that the dynamic AV delay interval is longer than the measured or predicted intrinsic conducted AV interval at each of the different heart rates or intervals, wherein automatically suggesting or automatically programming the dynamic AV delay interval to be longer than the measured or predicted intrinsic conducted AV interval at each of the different heart rates or intervals includes:
        determining a sensed AV offset using a difference between (1) a first time interval between an atrial paced contraction and a ventricular sensed contraction during at least one first cardiac cycle and (2) a second time interval between an atrial sensed contraction and a ventricular sensed contraction during at least one second cardiac cycle; and
        applying the determined sensed AV offset to the dynamic AV delay interval to obtain an AV-offset adjusted dynamic AV delay interval that is longer than the measured or predicted intrinsic conducted AV interval at each of the different heart rates or intervals.

21. The apparatus of claim 20, wherein the controller is configured to automatically suggest or program a dynamic AV delay that includes a safety margin by at least which the dynamic AV delay is longer than the measured or predicted conducted AV interval at each of the different heart rates or intervals.

22. The apparatus of claim 20, wherein the controller is configured to automatically suggest or automatically program an upper rate limit (URL) parameter using an age-predicted maximum heart rate or interval based on information about at least one of a patient's age or activity level, wherein the URL parameter includes at least one of a maximum tracking rate (MRT) or interval or a maximum sensing rate (MSR) or interval.

23. The apparatus of claim 20, wherein the controller is configured to determine a sensed AV offset using a difference between (1) a first time interval between an atrial paced contraction and a ventricular sensed contraction during at least one first cardiac cycle and (2) a second time interval between an atrial sensed contraction and a ventricular sensed contraction during at least one second cardiac cycle.

24. The apparatus of claim 23, wherein the controller is configured to apply the determined sensed AV offset to the dynamic AV delay interval to obtain an AV-offset adjusted dynamic AV delay interval that is longer than the measured or predicted intrinsic conducted AV interval at each of the different heart rates or intervals.

25. The apparatus of claim 20, wherein the controller is configured to determine a dynamic post ventricular atrial refractory period (PVARP), including:
to measure a retrograde conduction time between a ventricular paced contraction and a sensed atrial depolarization; and
to establish the dynamic PVARP to be greater than or equal to the measured retrograde conduction time, wherein the dynamic PVARP is used in determining the dynamic AV delay interval that is automatically suggested or automatically programmed to be longer than the measured or predicted intrinsic conducted AV interval at each of the different heart rates or intervals.

26. The apparatus of claim 25, wherein the controller is configured to determine an atrioventricular search hysteresis (AVSH) control parameter that controls providing an extended dynamic AV delay interval to allow an additional time period for ventricular sensing, and to constrain the AVSH control parameter by selecting the AVSH control parameter to limit the extended dynamic AV delay interval to be longer than a sum of a minimum value of the dynamic AV delay interval and a minimum value of the dynamic PVARP.

27. The apparatus of claim 26, comprising a display configured to graphically display to a user the AVSH interval as a function of heart rate or interval, together with the measured or predicted intrinsic conducted AV interval as a function of heart rate or interval.

28. The apparatus of claim 27, in which the display is configured to display to the user at least one of an indication of a safety margin by which the AVSH interval exceeds the measured or predicted intrinsic conducted AV interval or an indication of how much ventricular pacing is expected to occur.

29. The apparatus of claim 28, in which the display is configured to display to the user a suggested or programmed maximum tracking rate (MTR) or interval value, a minimum AV delay value, a maximum AV delay value, a sensed AV offset value, a minimum post ventricular atrial refractory period (PVARP) value, a maximum PVARP value, and an AV search hysteresis value.

30. A method of programming an implantable cardiac rhythm management device to avoid unnecessary ventricular pacing, the method comprising:
measuring an intrinsic conducted AV interval at a first heart rate or interval, wherein the intrinsic conducted AV interval is initiated by either a sensed or paced atrial contraction and is concluded by a sensed ventricular contraction;
measuring the first heart rate or interval;
automatically measuring or automatically extrapolating intrinsic conducted AV intervals at heart rates or intervals that are different from the first heart rate or interval to determine a measured or predicted intrinsic conducted AV interval as a function of different heart rates or intervals, wherein the automatically extrapolating includes using the measured intrinsic conducted AV interval at the measured first heart rate or interval and the measured first heart rate or interval for performing the extrapolating;
automatically suggesting or automatically programming a dynamic AV delay interval, based upon the measured or predicted intrinsic conducted AV interval as a function of the different heart rates or intervals, such that the dynamic AV delay interval is longer than the measured or predicted intrinsic conducted AV interval at each of the different heart rates or intervals;
displaying to a user an indication of an expected or actual amount of ventricular pacing for at least one heart rate or interval; and
allowing the user to drag-and-drop the automatically suggested or automatically programmed dynamic AV delay interval to adjust the automatically programmed dynamic AV delay interval.

31. The method of claim 30, comprising updating the expected or actual amount of ventricular pacing for at least the one heart rate or interval based on the user dragged-and-dropped dynamic AV delay interval.

* * * * *

UNITED STATES PATENT AND TRADEMARK OFFICE
CERTIFICATE OF CORRECTION

PATENT NO. : 7,636,598 B2 Page 1 of 1
APPLICATION NO. : 11/567924
DATED : December 22, 2009
INVENTOR(S) : Michael P. Husby It is certified that error appears in the above-identified patent and that said Letters Patent is hereby corrected as shown below:

In column 18, line 11, in Claim 6, delete "UIRL" and insert -- URL --, therefor.

In column 19, line 12, in Claim 18, delete "(MIRT)" and insert -- (MRT) --, therefor.

In column 19, line 14, in Claim 18, delete "Delay" and insert -- delay --, therefor.

In column 19, line 15, in Claim 18, delete "Sensed" and insert -- sensed --, therefor.

In column 19, line 15, in Claim 18, delete "Offset" and insert -- offset --, therefor.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,636,598 B2 | Page 1 of 1 |
| APPLICATION NO. | : 11/567924 | |
| DATED | : December 22, 2009 | |
| INVENTOR(S) | : Michael P. Husby | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 310 days.

Signed and Sealed this

Twenty-first Day of December, 2010

David J. Kappos
*Director of the United States Patent and Trademark Office*